(12) United States Patent
Collis (10) Patent No.: US 8,940,882 B2
(45) Date of Patent: Jan. 27, 2015

(54) MULTIPLE FLUOROPHORE DETECTOR SYSTEM

(75) Inventor: Matthew Collis, Seven Valleys, PA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1634 days.

(21) Appl. No.: 11/785,441

(22) Filed: Apr. 18, 2007

(65) Prior Publication Data

US 2011/0223592 A1    Sep. 15, 2011

Related U.S. Application Data

(63) Continuation of application No. 10/825,943, filed on Apr. 14, 2004, now abandoned.

(51) Int. Cl.
*C07H 21/04* (2006.01)
*C12Q 1/68* (2006.01)

(52) U.S. Cl.
CPC .................................. *C12Q 1/6816* (2013.01)
USPC ............................. 536/23.1; 536/24.3; 435/6

(58) Field of Classification Search
None
See application file for complete search history.

(56) References Cited

U.S. PATENT DOCUMENTS

| | | |
|---|---|---|
| 5,270,184 A | 12/1993 | Walker et al. |
| 5,455,166 A | 10/1995 | Walker |
| 5,547,861 A | 8/1996 | Nadeau et al. |
| 5,550,025 A | 8/1996 | Walker |
| 5,593,867 A | 1/1997 | Walker et al. |
| 5,607,924 A | 3/1997 | Magda et al. |
| 5,798,491 A | 8/1998 | Magda et al. |
| 5,846,726 A * | 12/1998 | Nadeau et al. ............ 435/6.12 |
| 5,863,736 A | 1/1999 | Haaland |
| 5,919,630 A | 7/1999 | Nadeau et al. |
| 6,054,729 A | 4/2000 | Berenz |
| 6,066,458 A | 5/2000 | Haaland et al. |
| 6,216,049 B1 | 4/2001 | Yang et al. |
| 6,403,311 B1 * | 6/2002 | Chan .......................... 435/6.16 |
| 6,416,953 B1 * | 7/2002 | Heller ......................... 435/6.12 |
| 2004/0133313 A1 | 7/2004 | Kuhn |

FOREIGN PATENT DOCUMENTS

| | | |
|---|---|---|
| EP | 1 158 449 | 11/2001 |
| EP | 0 684 315 | 6/2002 |
| EP | 0 878 554 | 2/2007 |
| JP | 11-123083 A | 5/1999 |
| WO | 2004/027081 A2 | 4/2004 |

OTHER PUBLICATIONS

Crocket et al(analytical biochemistry (2001) vol. 290, pp. 89-97.*
Office Action from Japanese Patent Application No. 2005-116781 mailed on Jan. 4, 2011.
Morrison, et al., "Solution-Phase Detection of Polynucleotide Using Interacting Fluorescent Labels and Competitive Hybridization," *Analytical Biochemistry*, 1989, vol. 183, pp. 231-244.
Tyagi, et al., "Molecular Beacons: Probes that Fluoresce upon Hybridization," *Nature Biotech.* 1996, vol. 14, pp. 303-308.
Ghosh, et al., "Real Time Kinetics of Restriction Endonuclease Cleavage Monitored by Fluorescence Resonance Energy Transfer," *Nucleic Acids Research*, 1994, vol. 22, No. 15, pp. 3155-3159.
D. Freifelder, *Biophysical Chemistry*, 1976, W.H. Freeman and Company, San Francisco, pp. 426-428.
Sambrook et al., *Molecular Cloning: A Laboratory Manual*, 3rd ed., 2001, Cold Spring Harbor Press, Chapter 10, pp. 10.11-10.52.

* cited by examiner

*Primary Examiner* — Steven Pohnert
(74) *Attorney, Agent, or Firm* — Lerner, David, Littenberg, Krumholz & Mentlik, LLP (57) ABSTRACT

A detector oligonucleotide comprises multiple pairs of a donor fluorophore and a quencher molecule, which donor fluorophores and quencher molecules are separated by a site that is capable of being cleaved when in double-stranded form. The detector oligonucleotide may be made double-stranded in a manner that depends on the presence of a target nucleic acid, allowing the cleavage sites to be cleaved. Separation of the donor fluorophores and the quencher molecules decreases fluorescence quenching and generates a detectable change in a fluorescence parameter of the fluorophores of the detector oligonucleotide. By using multiple donor/quencher pairs, the present detector oligonucleotide advantageously generates a high signal to noise ratio and high efficiency in detection of a target nucleic acid.

20 Claims, 7 Drawing Sheets

MULTIPLE FLUOROPHORE DETECTOR SYSTEM

CLAIM FOR PRIORITY

This application claims priority to U.S. patent application Ser. No. 10/825,943, filed Apr. 14, 2004, now pending, which is herein incorporated by reference in its entirety.

FIELD OF THE INVENTION

The present invention relates generally to methods for detecting nucleic acid target sequences. In particular, the present invention relates to a detector oligonucleotide comprising multiple fluorophores that is useful for highly sensitive detection of nucleic acids.

BACKGROUND OF THE INVENTION

The identification of unique DNA or RNA sequences or specific genes within a biological sample may indicate the presence of a physiological or pathological condition, such as cancer or a pathogen infection. For example, nucleic acid hybridization assays may be used in the agriculture and food processing industries to detect plant pathogens or harmful bacteria.

Luminescent labels, which emit light upon excitation by an external energy source, have proven useful to detect nucleic acid molecules and to probe the interaction between these molecules. These labels are categorized by the source of the exciting energy, such as, for example: (1) photoluminescent or fluorescent labels, which are excitable by units of electromagnetic radiation of infrared, visible or ultraviolet light; (2) chemiluminescent labels, which obtain energy from chemical reactions; (3) radioluminescent labels, which are excitable by energy from high energy particles; and (4) bioluminescent labels, which are excitable by energy supplied in a biological system. The use of luminescent labels permits "homogeneous" assay techniques in which a probe labeled with a luminescent label exhibits different luminescent characteristics when associated with a target, thereby obviating the need to remove unassociated labeled probe. See, e.g., Morrison et al., *Anal. Biochem.* 183: 231 (1989).

Luminescent labels also have proven useful in nucleic acid amplification techniques. Luminescent signal primers (also referred to as "detector probes"), which hybridize to a target sequence downstream of the hybridization site of amplification primers, have been described for use in detection of nucleic acid amplification. See, e.g., U.S. Pat. No. 5,547,861, which is incorporated by reference herein. A signal primer is extended by polymerase in a manner similar to extension of the amplification primers. Extension of the amplification primer displaces the extension product of the signal primer in a target amplification-dependent manner, producing a detectable double-stranded secondary amplification product that indicates target amplification. The secondary amplification products generated from signal primers may be detected by various means, as exemplified in U.S. Pat. No. 5,550,025 (incorporation of lipophilic dyes and restriction sites) and U.S. Pat. No. 5,593,867 (fluorescence polarization detection), which are incorporated by reference herein.

Fluorescence energy transfer has been used advantageously to probe the interaction between complementary nucleic acids in various hybridization methods. Fluorescent energy transfer occurs between a donor fluorophore and a quencher molecule (which may or may not be a fluorophore) when the absorption spectrum of the quencher overlaps the emission spectrum of the donor and the two are in sufficiently close proximity. The excited-state energy of the donor is transferred by a resonance dipole-induced dipole interaction to the neighboring quencher, resulting in quenching of donor fluorescence. In some cases, if the quencher is also a fluorophore, the intensity of its fluorescence may be enhanced. The efficiency of energy transfer depends on the distance between the donor and quencher in a manner well known in the art.

Probes or primers comprising intramolecularly base-paired secondary structures capable of exhibiting changes in fluorescence quenching recently have been employed for detection of nucleic acid target sequences. In these systems, a donor and a quencher fluorophore, which are in close proximity in the base-paired secondary structure of the probe or primer, become spatially separated due to unfolding of the secondary structure because of base-pairing with a target. The target-dependent separation of the two fluorophores reduces quenching of the donor fluorophore, which increases the fluorescence intensity of the donor. For example, a self-complementary oligonucleotide labeled with fluorophores at its 5' and 3' ends forms a hairpin that brings the two fluorophores into close proximity so that energy transfer and quenching can occur. Hybridization of the self-complementary oligonucleotide to its complement on a target oligonucleotide disrupts the hairpin and increases the distance between the two fluorophores, thereby reducing quenching. Hairpin structures labeled in this manner are described by Tyagi et al., *Nature Biotech.* 14: 303-308 (1996), for example.

A disadvantage of the hairpin structure is that it is very stable, and conversion to the unquenched, hybridized form is often slow and only moderately energetically favored. In the case of the structures disclosed in Tyagi et al., supra, for example, the target sequence, must compete for hybridization with the complementary sequence that forms the hairpin structure, thereby lowering performance.

A partially single-stranded, partially double-stranded signal primer labeled with a donor/quencher pair has also been described. For example, EP 0 878 554 discloses a signal primer with a donor/quencher pair flanking a single-stranded restriction endonuclease recognition site. In the presence of the target, the restriction site becomes double-stranded and cleavable by a restriction endonuclease. Cleavage separates the donor/quencher pair to decrease donor quenching.

Other methods have employed restriction endonuclease sites to separate a donor/acceptor pair. Japanese Patent No. 93015439 B discloses methods for measuring polynucleotides by hybridizing a single-stranded target to a single-stranded polynucleotide probe labeled with an energy transfer pair. The double-stranded hybrid is then cleaved between the labels by a restriction enzyme, and fluorescence of one of the labels is measured. A disadvantage of this method is that the restriction site in the probe must also be present in the target sequence being detected. Ghosh et al., *Nucl. Acids Res.* 22: 3155-3159 (1994) describe restriction enzyme-catalyzed cleavage of a fluorophore-labeled oligonucleotide, which is analyzed using fluorescence resonance energy transfer. In this assay, a labeled oligonucleotide is hybridized to a complementary sequence that also is labeled to produce a cleavable double-stranded restriction site. A disadvantage of this method is the requirement to modify each of the two strands with a fluorescent label.

A donor/acceptor pair also has been used in amplification methods, such as a strand-displacement amplification (SDA) method described in U.S. Pat. Nos. 5,919,630; 5,846,726; and 6,054,729, which are herein incorporated by reference in their entirety. These patents disclose a single-stranded signal primer that is modified by linkage to a donor/acceptor pair.

The signal primer may further comprise a restriction endonuclease recognition site between the donor and acceptor. When the signal primer forms a duplex with a complementary target sequence, the restriction endonuclease recognition site is rendered double-stranded and cleavable or nickable by a restriction endonuclease. Cleavage or nicking separates the donor and acceptor, and a change in fluorescence due to decreased quenching is detected as an indication of target sequence amplification.

There remains a need for improved methods for detection of nucleotide sequences. Specifically, there is a need to improve the ratio between a fluorescence signal indicative of target amplification and a background signal created by light scattering and non-quenched fluorescence. There also is a need for more efficient means of amplification detection and greater sensitivity of fluorescent detection methods.

SUMMARY OF THE INVENTION

The present invention meets these needs by providing a detector oligonucleotide that comprises multiple pairs of a donor fluorophore and a quencher molecule, which pairs are separated by a cleavage site that is capable of being enzymatically or chemically cleaved. The detector oligonucleotide of the present invention may be used with amplification in a homogenous assay system to detect a nucleotide sequence, or the detector oligonucleotide may be used in a heterologous assay system without amplification. The use of multiple donor/quencher pairs increases the ratio between a fluorescence signal indicative of target amplification and a background signal, thereby increasing both the sensitivity and efficiency of detection. An additional benefit is achieved by using multiple fluorophores on the same detector oligonucleotide. Namely, the amplification reaction is more efficient because only one complementary adapter molecule is required to extend the detector oligonucleotide. In addition, less detector oligonucleotide is required to generate the same signal as other detectors.

A fluorophore donor of the present detector oligonucleotide is sufficiently close to a quencher molecule for energy transfer to occur between the donor and quencher. The donor/quencher pair in one embodiment may be separated by as few nucleic acid bases as possible to accommodate the cleavage site. Various configurations of donor and quencher molecules are possible. For example, but not by way of limitation, a donor fluorophore may be configured between two or more quenching molecules, or a quenching molecule may be configured between two or more donor fluorophores.

In one embodiment, the detector oligonucleotide is single-stranded and comprises multiple pairs of a donor fluorophore and a quencher molecule, where the donor fluorophore and the quencher molecule in each pair are separated by a site that is cleavable when the detector oligonucleotide forms a duplex with a second oligonucleotide. The second oligonucleotide in this embodiment is capable of being formed in the presence of a target nucleic acid.

The detector oligonucleotide may comprise polynucleotides having one or more chemical modifications, such as a linker moiety, to allow attachment of the donor and quencher molecules. The backbone of the detector oligonucleotide may have branched structures so that the detector oligonucleotide may accommodate additional donor/quencher pairs.

In another aspect of the present invention, a method is provided for detecting a target nucleic acid in a sample using a detector oligonucleotide of the present invention. The method comprises contacting a detector oligonucleotide (i.e., a "first oligonucleotide") with a second oligonucleotide to form a duplex between the first and second oligonucleotides. The first oligonucleotide comprises multiple pairs of donor fluorophores and quencher molecules, where the donor fluorophores and the quencher molecules in each pair are separated by a cleavage site. The presence of the second oligonucleotide is indicative of the presence of the target nucleic acid. The cleavage sites are double-stranded in the duplex formed by the first and second oligonucleotides, which allows the cleavage sites to be cleaved to generate a signal. Detection of a change in a fluorescence parameter of the donor fluorophores following cleavage indicates the presence of the target nucleic acid. One skilled in the art would readily appreciate that the target nucleic acid may need to be dissociated from a duplex prior to duplex formation with the detector oligonucleotide.

Detection of the donor fluorophores may comprise monitoring the extent and/or rate of change of fluorescence. In one embodiment, the change of the fluorescence emission of the donor is monitored to indicate the presence or absence, or to provide an estimated number, of the target nucleic acids in the sample. The monitoring step can likewise be performed by measurement of, among other things, a change in the extent and/or rate of change of the fluorescence emission of a quencher molecule that is also a fluorophore.

In yet another aspect of the present invention, a kit is provided that comprises a detector oligonucleotide according to the present invention. The kit may also comprise additional components, such as internal standards, controls, enzymes capable of amplifying nucleic acids, chemical reagents, fluorophores and/or quenchers that can be attached to a detector oligonucleotide, as well as instructions for using the kit to detect a target nucleic acid. The kit, for example, but not by way of limitation, may further comprise an adapter oligonucleotide that comprises a first portion, which is capable of forming a duplex with the complement of a target oligonucleotide, and a second portion, the complement of which is capable of forming a duplex with the first portion of the detector oligonucleotide.

Other features and advantages of the present invention will be apparent from the following drawings and description of the preferred embodiments and also from the appended claims.

DETAILED DESCRIPTION OF THE INVENTION

The present invention employs a detector oligonucleotide to detect a target nucleic acid. A detector oligonucleotide comprises multiple pairs of donor fluorophores and quencher molecules, which provide an improved fluorescence signal to background ratio and more efficient detection of a target nucleic acid. For the purpose of the invention, "multiple pairs of donor fluorophores and a quencher molecules" is synonymous with "multiple donor/quencher pairs." A donor fluorophore and a quencher molecule in a donor/quencher pair are separated by a cleavable site. In one embodiment, the site is cleavable when the detector oligonucleotide forms a duplex with a second oligonucleotide, which is formed in the presence of a target nucleic acid.

A donor/quencher pair of the present invention comprises a "donor fluorophore" and a "quencher molecule." A donor fluorophore in an excited state is sensitive to the presence of a quencher molecule in close proximity to the donor. That is, the quencher molecule acts as an acceptor of resonance energy that is transferred from the donor, provided the two are in close proximity. A quencher molecule need not be a fluorophore to be an acceptor of resonance energy. Energy transfer can occur between a fluorophore and a quencher molecule, provided that the two are separated by a distance on the order of tens of Angstroms (e.g., within about 60 Å), and provided that the donor fluorescence emission spectrum overlaps significantly with the absorption spectrum of the quencher molecule. The term "close proximity" is herein defined as the distance between donor and acceptor molecules that is sufficient for a detectable change in a fluorescence parameter once the donor and quencher are separated.

A detectable change in a fluorescence parameter is monitored as an indication of the presence of the target sequence. A "fluorescence parameter" includes, but is not limited to, an increase in donor fluorescence intensity, a decrease in quencher fluorescence intensity (when the quencher molecule is a fluorophore), a rate of change of fluorescence intensity, a ratio of fluorescence before and after cleavage, or a combination thereof. Monitoring a change in donor fluorescence intensity is preferred because this change is typically larger than the change in quencher fluorescence intensity. Other fluorescence parameters that may be used to detect a change in an interaction between the donor and quencher include, but are not limited to, a change in polarization anisotropy (to measure the relative change in fluorophore mobility before and after cleavage) or a wavelength shift in an excitation or emission spectrum. In one embodiment, an algorithm may be used to analyze the change in one or more fluorescence parameters. See U.S. Pat. No. 6,216,049 and No. 5,863,736, herein incorporated by reference.

Suitable fluorophores for the invention include, but are not limited to, fluorescein, sulforhodamine 101, pyrenebutanoate, acridine, ethenoadenosine, eosin, rhodamine, and erythrosin. Many donor/quencher pairs are known in the art and are useful in the present invention. These include, but are not limited to, fluorescein isothiocyanate (FITC)/tetramethylrhodamine isothiocyanate (TRITC), FITC/Texas Red™ (Molecular Probes), FITC/N-hydroxysuccinimidyl-1-pyrenebutyrate (PYB), FITC/eosin isothiocyanate (EITC), N-hydroxysuccinimidyl-1-pyrenesulfonate (PYS)/FITC, FITC/Rhodamine X, and FITC/tetramethylrhodamine (TAMRA), fluorescein/Rhodamine X, Rhodamine X/Cy5, or fluorescein/P-(dimethyl aminophenylazo) benzoic acid (DABCYL). Non-fluorescent quencher molecules, such as DABCYL, DAMBI, DABSYL or methyl red, are particularly useful. DABCYL is a non-fluorescent quencher dye that effectively quenches fluorescence from an adjacent fluorophore, e.g., fluorescein or 5-(2'-aminoethyl)aminonaphthalene (EDANS). In one embodiment, the donor and the quencher are the same fluorophore, wherein the fluorophore has overlapping adsorption and emission spectra. Certain donor/quencher pairs are noted in the specification and in the following examples; however, those skilled in the art will appreciate that other pairs are useful in the present invention. That is, the selection of a particular donor/quencher pair is not critical to the present invention. In a donor/quencher pair useful for the present invention, the emission wavelengths of the donor fluorophore sufficiently overlaps the excitation wavelengths of the quencher molecule to allow efficient energy transfer, charge transfer or fluorescence quenching. The donor and quencher may be linked at their respective sites in the detector oligonucleotide using routine terminal and internal labeling methods that are known in the art.

In addition to the use of donor fluorophores as a means for detecting a polynucleotide target, the use of other luminescent labels, particularly chemiluminescent agents, is also within the present invention.

The terms "target" or "target nucleic acid" refer to nucleic acids to be detected, which may be RNA or DNA having any of the configurations of these molecules that are encountered, such as mRNA and genomic DNA. For instance, the target nucleic acid may be single-stranded or double-stranded, or it may have secondary structure. The target of a double-stranded nucleic acid is the strand for which detection is sought. The artisan will appreciate that, when detection requires the formation of a duplex with a double-stranded target nucleic acid or a target nucleic with secondary structure, detection will be facilitated by making the target nucleic acid single-stranded. For the purpose of the invention, the target nucleic acid may be isolated or naturally occurring, and it may be detected in vitro or in situ. In one embodiment of the invention, a method of detecting a target nucleic acid comprises an amplification reaction that is catalyzed by a DNA polymerase. The templates for amplification encompassed by the present invention include the target nucleic acid itself, a complementary strand of a target nucleic acid, and either strand of a copy of the original sequence that is produced by replication or amplification. The target nucleic acid also may be a template for extension from a template of a hybridized primer. In one embodiment, the target nucleic acid is derived from a pathogen.

"Cleavage" of an oligonucleotide refers to breaking of the phosphodiester bonds of both strands of a DNA or RNA duplex or to breaking of the phosphodiester bond of single-stranded DNA or RNA. This is in contrast to "nicking," which refers to breaking the phosphodiester bond of only one of the two strands in a DNA or RNA duplex. The cleavage site between the donor fluorophore and the quencher may be cleaved when the site is in a double-stranded form. A "cleavage site" is a stretch of bases of a double-stranded nucleic acid that is specifically cleaved by a cleavage reagent. In one embodiment, a cleavage site is a recognition site for a restriction endonuclease. Various recognition sites for restriction endonucleases are well known in the art. Suitable cleavage reagents also include chemical cleavage reagents that cut both strands of a cleavage site. For example, but not by way of limitation, a site-specific photoactivated cleavage reagent of the type described in U.S. Pat. Nos. 5,798,491 and 5,607,924, which are herein incorporated by reference, could be used.

The change in fluorescence intensity upon cleavage of the detector oligo-nucleotide depends on the distance separating the donor fluorophore and quencher molecule in the uncleaved detector oligonucleotide. See U.S. Pat. No. 5,919,630. The efficiency of energy transfer is governed by the following equation:

$$E = \frac{R_o^6}{(R_o^6 + R^6)}$$

where r is the distance between the donor and quencher, and $R_o$ is a constant related to each donor/quencher pair that can be calculated from certain parameters of the adsorption and emission spectra of each, according to well known methods.

See BIOPHYSICAL CHEMISTRY, D. Freifelder, ed., W.H. Freeman and Company, San Francisco (1976) at page 426-28, herein incorporated by reference.

In general, the magnitude of the change in donor emission following double-stranded cleavage increases with decreasing distance between the donor and quencher in the intact, detector oligonucleotide. The distance between the donor and the quencher, however, may be adjusted to provide greater efficiency of cleavage. For example, but not by way of limitation, if a restriction endonuclease recognition site is used as the cleavage site, the separation between the donor and the quencher can be adjusted to accommodate binding of the restriction endonuclease to its recognition site, thereby avoiding or limiting steric hindrance that may otherwise interfere with complete cleavage. In one embodiment, the donor fluorophore and the quencher molecule are separated by about 5-20 nucleotides, or preferably by about 6-8 nucleotides.

The skilled artisan will realize that the advantages of the present detector oligonucleotide may be retained while modifying various aspects of its structure. For example, but not by way of limitation, the number of donor/quencher pairs may be modified. The addition of more donor/quencher pairs to the detector oligonucleotide is expected to increase the amount of total fluorescence observable after cleavage of the double-stranded cleavage site. There is no upper limit to the number of donor/quencher pairs that may be added to the detector oligonucleotide. In one embodiment, the number of donor/quencher pairs is at least two. In other embodiments, the detector oligonucleotide contains at least three or more donor/quencher pairs. In other embodiments, the detector oligonucleotide may contain at least 10, 20, 30, or 50 pairs, or it may contain hundreds of donor/quencher pairs, as needed to produce an optimal signal-to-noise ratio and assay sensitivity.

In some embodiments, the length of the oligonucleotide needed to accommodate the donor/quencher pairs will exceed 200, or even 500 or more, bases. Further, the oligonucleotide backbone of the detector may contain branches to provide additional oligonucleotide sequences that may contain donor/quencher pairs. Methods to create branched or multiple-branched oligonucleotides are well-known in the art. Accordingly, an "oligonucleotide" as used herein is not limited to a linear nucleic acid of about 2-20 nucleotides in length.

Further, the manner or order in which the donor/quencher pairs is arranged is not critical to the invention. For example, but not by way of limitation, the donor fluorophore ("D") and the quencher molecule ("Q") may be ordered as D/Q, D/Q or they may be ordered as Q/D, D/Q, D/Q/D, Q/D/Q, provided that donor fluorophore is in close proximity to the quencher molecule. In one embodiment, donors and quenchers may be configured in the sequence D/QQQ/D or Q/DDD/Q. In these embodiments, the cleavage site between the donor and quencher is indicated by the slash mark. Accordingly, for the purpose of the invention, a "donor/quencher pair" comprises a donor fluorophore in close proximity to a quencher molecule, where the donor and the quencher are separated by a cleavage site, and it may include additional donor fluorophores or quencher molecules in close proximity to either the donor or the quencher that are adjacent to the cleavage site. A configuration having three donors and quenchers and two cleavage sites, such as D/Q/D or Q/D/Q, is defined as two "donor/quencher pairs," even though each pair shares either a donor fluorophore or a quencher molecule.

In one embodiment of the invention, the detector oligonucleotide is used in a method of detecting a target nucleic acid that comprises the use of the detector oligonucleotide in an amplification reaction. Various methods of nucleic acid amplification are known in the art and are applicable to the present invention including, but not limited to, strand displacement amplification (SDA), polymerase chain reaction (PCR), ligase chain reaction, self-sustained sequence replication (3SR), Q beta replicase-based amplification, solid phase amplification, nucleic acid sequence-based amplification (NASBA), rolling circle amplification, and transcription mediated amplification (TMA).

An "amplification primer" is a primer for amplification of a target sequence by primer extension. For example, in SDA, the 3' end of an amplification primer hybridizes at the 3' end of the target nucleic acid. The amplification primer comprises a recognition site near its 5' end for a restriction endonuclease that will allow a DNA or an RNA duplex to be nicked when the recognition site is hemimodified, as described in U.S. Pat. Nos. 5,455,166; 5,270,184; and EP 0 684 315, which are herein incorporated by reference with respect to the use of heznimodified restriction sites in an SDA reaction. The amplification primer also is extendible from its 3' terminus by DNA polymerase when the target binding sequence of the amplification primer is hybridized to the target nucleic acid. The amplification primer may be used in a reaction that results in exponential amplification of the target nucleic acid.

Amplification primers for PCR may consist only of target binding sequences because no special sequences or structures are required to drive the amplification reaction. By contrast, amplification primers useful for other amplification methods, such as 3SR and NASBA, comprise an RNA polymerase promoter near the 5' end. The promoter is appended to the target nucleic acid by duplex formation between the primer and the target nucleic acid and serves to drive the amplification reaction by directing transcription of multiple RNA copies of the target. Other amplification primers known in the art may also be useful for the invention.

"Extension products" are nucleic acids that comprise a primer, or a portion of a primer, and a newly synthesized strand that is the complement of the target nucleic acid downstream of the primer binding site. Extension products result from hybridization of a primer to a target sequence and extension of the primer by polymerase using the target nucleic acid as a template.

One of skill in the art will understand that "hybridization" and "duplex formation" as used herein do not require a precise base-for-base complementarity. That is, a duplex can form, between two nucleic acids that contained mismatched base pairs. The conditions under which nucleic acids that are perfectly complementary or that contain mismatched base pairs will hybridize to form a duplex are well known in the art and are described, for example, in MOLECULAR CLONING: A LABORATORY MANUAL, $3^{rd}$ ed., Sambrook et al., eds., Cold Spring Harbor Press, Cold Spring Harbor (2001) at Chapter 10, which is herein incorporated by reference.

Figure 1:
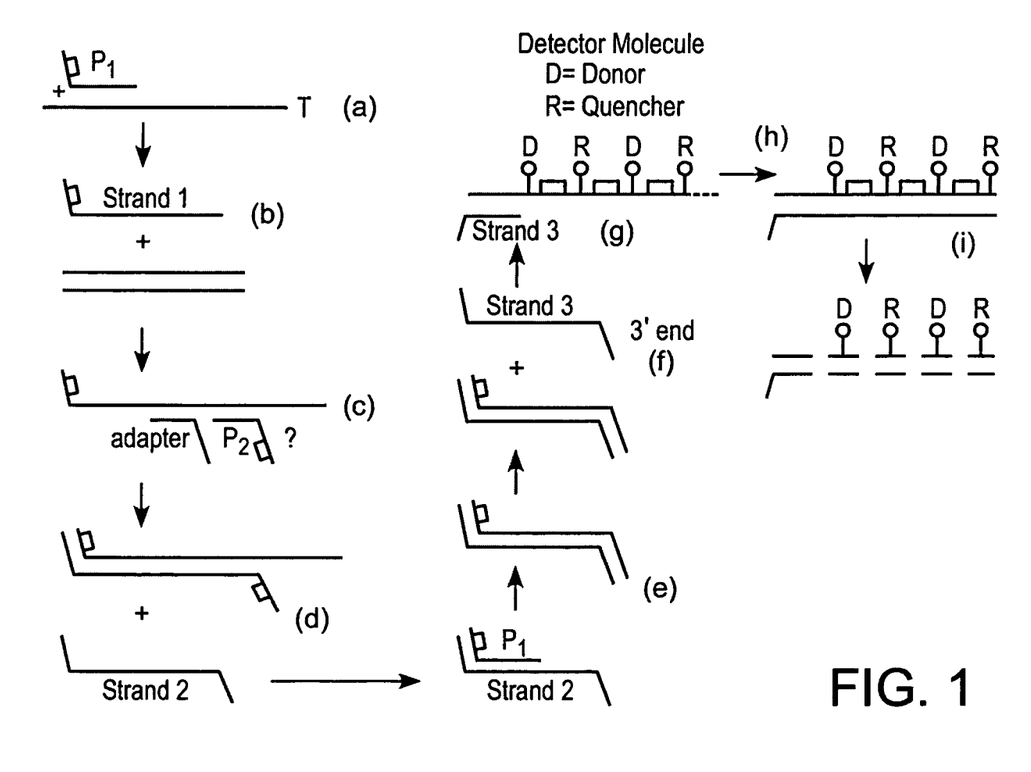
FIG. 1 illustrates the use of the detector oligonucleotide of the invention in an amplification reaction for detection of a target sequence.
Figure 2A:
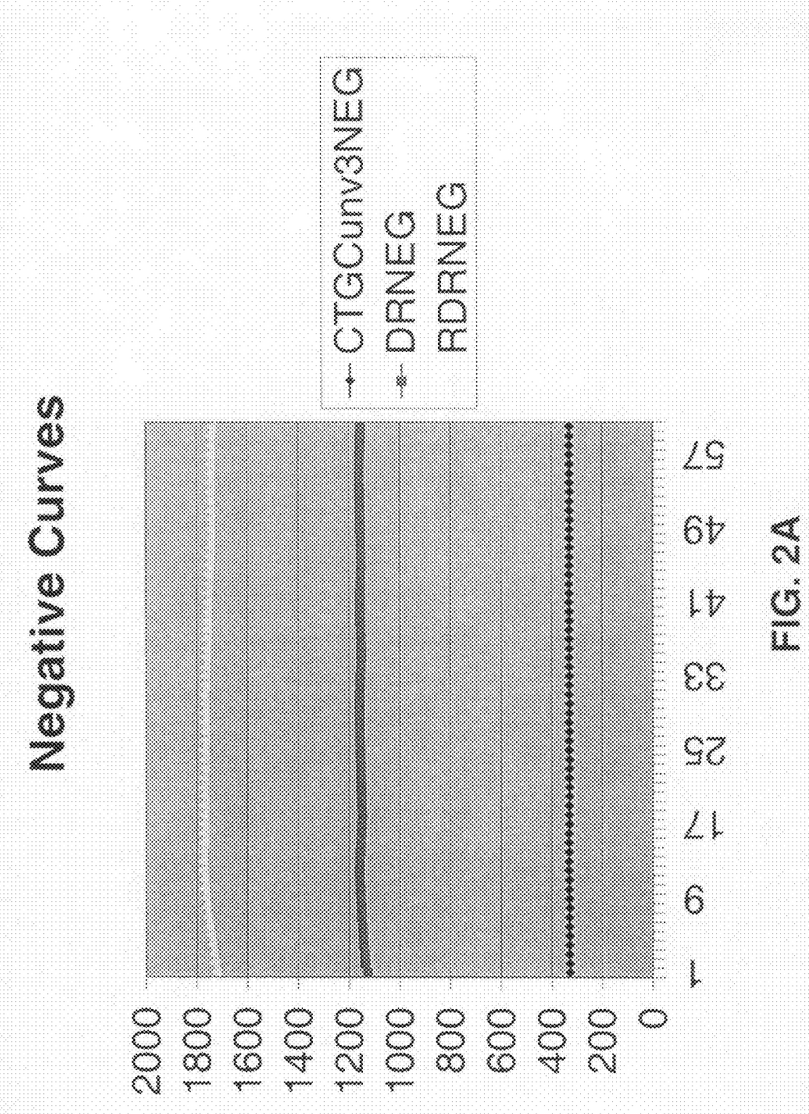
FIGS. 2A-2F are graphs showing the results of the experiments conducted in Example 2, wherein a detector oligonucleotide of the invention is compared to previously known detector probes.
Figure 2B:
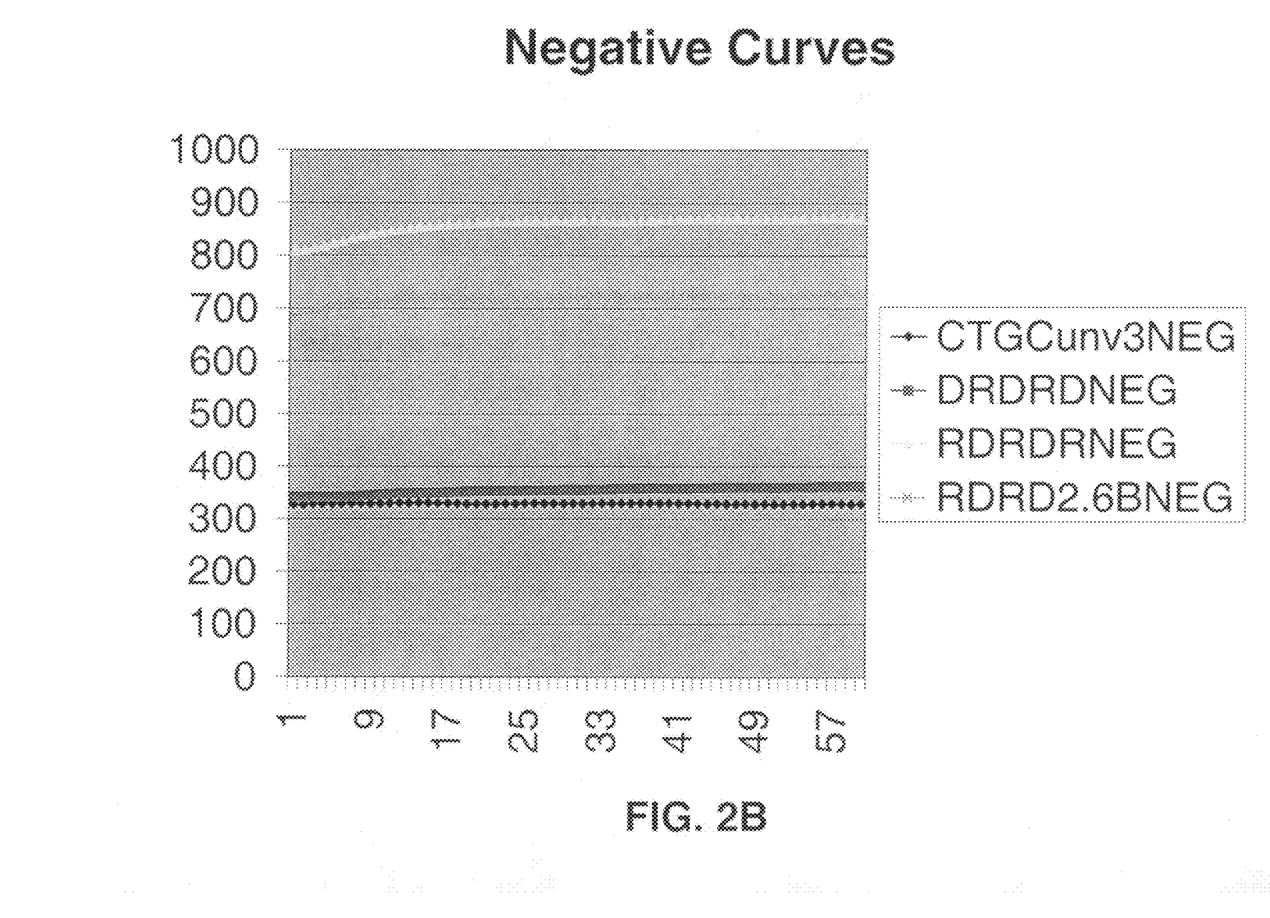
Figure 2C:
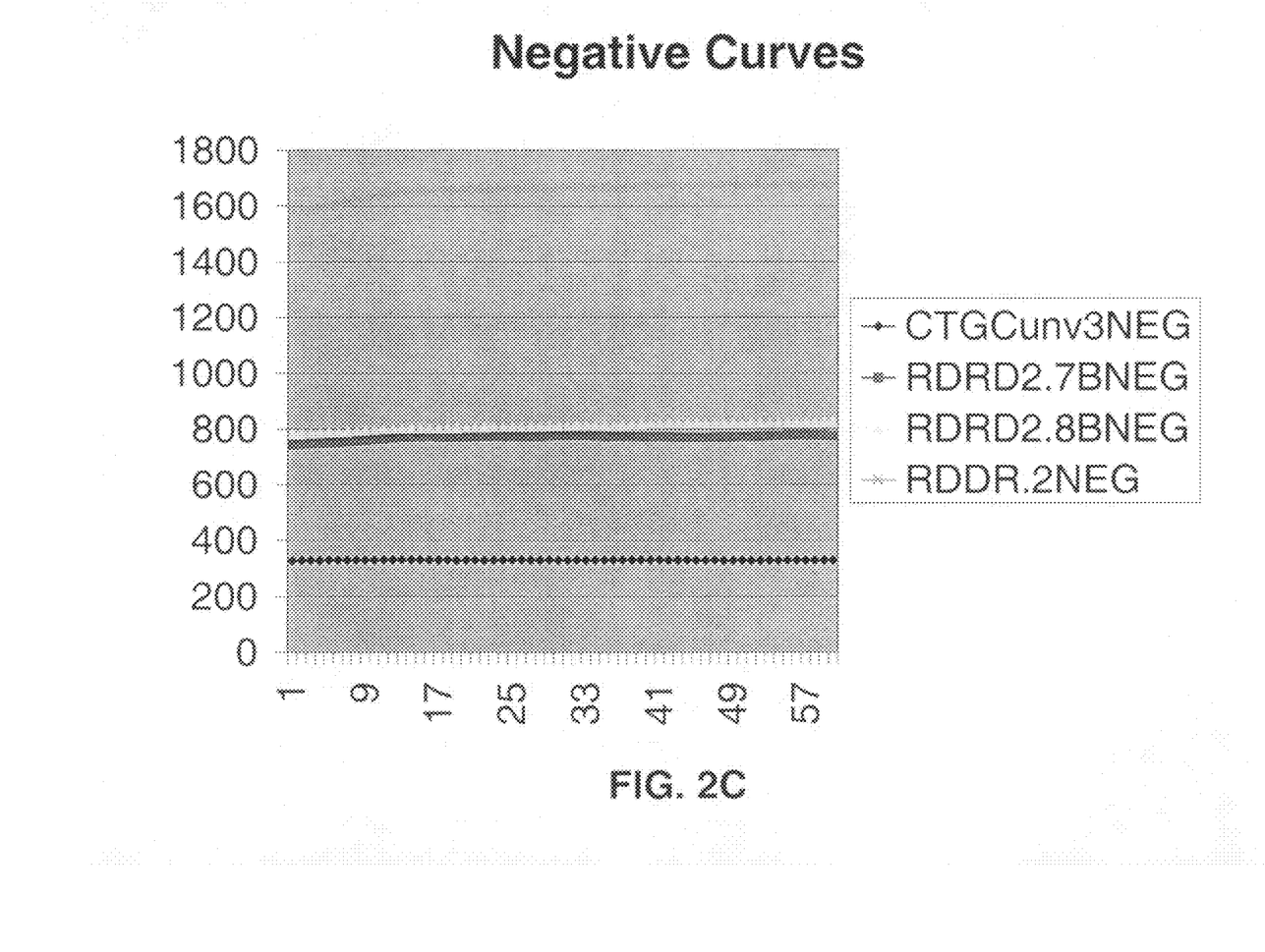
Figure 2D:
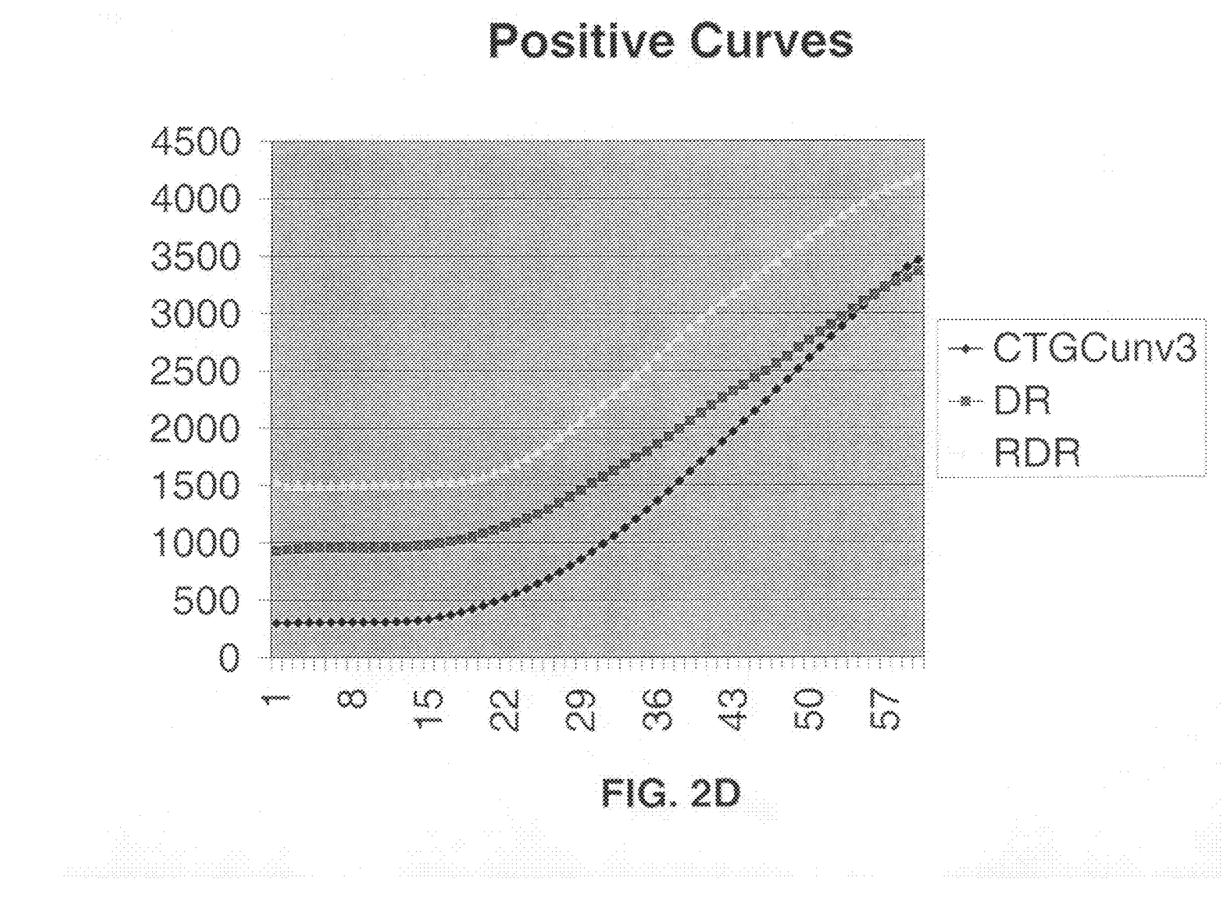
Figure 2E:
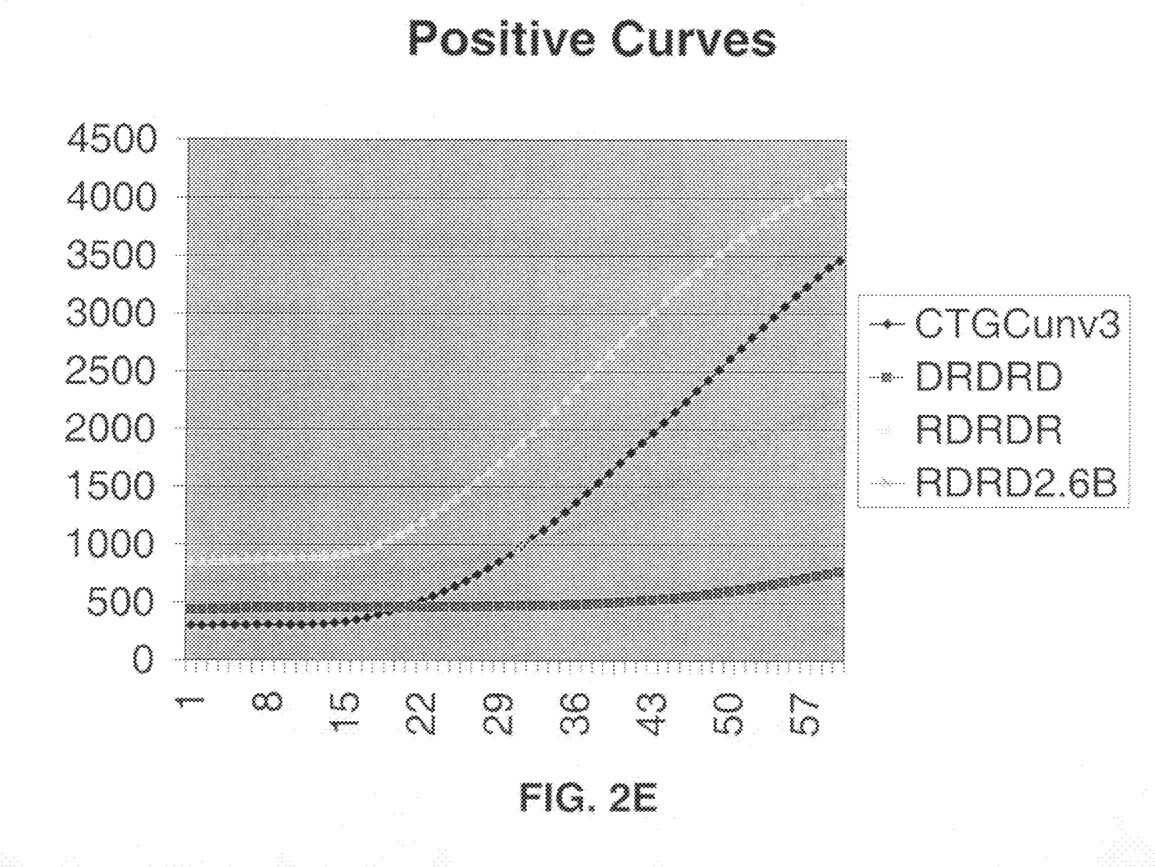
Figure 2F:
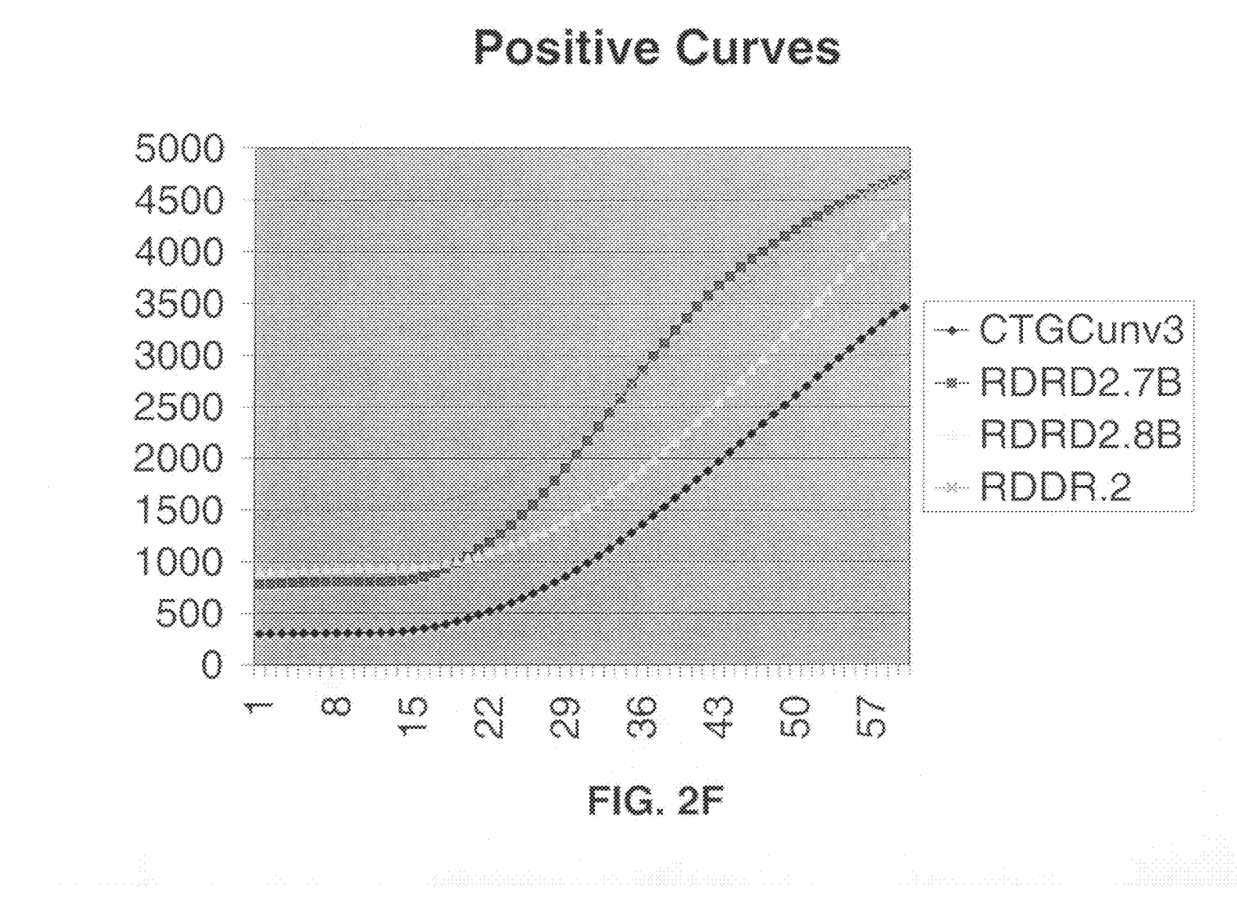

FIG. 1 illustrates the reaction involving a detector oligonucleotide of the invention. A primer, $P_1$, hybridizes to a target nucleic acid, T. DNA polymerase (present step a) extends a complimentary strand from $P_1$ to form strand 1. An oligonucleotide "bumper" $B_1$ binds upstream of $P_1$. The primer P1 and bumper B1 are typically added together, but may be added separately. When a polymerase extends a complimentary strand from $B_1$, strand 1 is removed from the target strand, T (step b). Primer $P_2$ then hybridizes to strand 1, an adapter oligonucleotide hybridizes downstream of $P_2$, and both are extended by a polymerase (step c). The strand extended from $P_2$, strand 2, bumps the strand extended from the adapter oligonucleotide (step d). $P_1$ now hybridizes to strand 2, and the strand is extended again (step e). The $P_1$-extended strand is nicked at a restriction endonuclease site located its 5' end, and the strand is amplified by SDA to form strand 3 (step f). Steps (a) through (f) result in multiple copies of strand 3 from a single target-specific hybridization event initiated by $P_1$.

Hybridization of strand 3 to the multiple detector oligonucleotide forms an initiation template for polymerase extension, which converts the detector oligonucleotide to a double-stranded, cleavable form. Specifically, strand 3 forms a duplex at its 3' end with a complimentary sequence on the multiple detector oligonucleotide (step g). Once extended by polymerase (step h), the multiple detector oligonucleotide will be cleaved with a restriction endonuclease (step i). Restriction endonuclease recognition sites are located between donor fluorophore and quencher molecule on the detector oligo-nucleotide, such that digestion with a restriction endonuclease results in the physical separation of the donor and quencher. The separation of donor and quencher results in the increased florescence of the donor, thereby indicating the presence of the target, T.

The signal may be detected at a selected endpoint in the reaction or in real time. For example, but not way of limitation, the signal may be detected by amplifying strand 3 concurrently with an extension reaction of the hybrid between strand 3 and the multiple detector oligonucleotide. Such homogeneous real-time assays may be used to provide semi-quantitative or quantitative information about the initial amount of target present. That is, when more initial copies of the target sequence are present, fewer rounds of amplification are required to produce a fluorescence signal above a threshold signal level. The initial amount of target nucleic acid in this type of assay is determined by comparison of the experimental results to results for a known amount of purified target nucleic acid. Methods for analyzing readings of assays are also found in U.S. Pat. Nos. 6,216,049; 6,066,458; and 5,863,736; U.S. patent application Ser. Nos. 10/626,582; and 09/574,031, which corresponds to European Application No. EP 1158449, published Nov. 28, 2001, the contents of each of which are herein incorporated by reference.

As described above, the signal may be amplified by generating multiple copies of strand 3 through a target-dependent amplification reaction using primer 1, primer 2 and an adaptor primer. Alternative amplification methods that are known in the art, such as those set forth above, may be used to produce an equivalent of strand 3 that can be used in the present invention.

The detector oligonucleotide alternatively may be used to detect a target nucleic acid without amplification reaction. For example, but not by way of limitation, the detector oligonucleotide may comprise a region that hybridizes directly with the target nucleic acid. In this embodiment, the detector oligonucleotide may be partially double-stranded, provided that it comprises a single-stranded portion that is capable of forming a duplex with a target nucleic acid. In another embodiment, the detector oligonucleotide may be entirely or substantially single-stranded, and the detector oligonucleotide is made double-stranded by a polymerase extension reaction that is initiated at the duplex formed between the detector oligonucleotide and the target nucleic acid. This duplex may be formed, for example, but not by way of limitation, between a 5' portion of the detector and a 3' portion of a fragment of the target nucleic acid that has been generated by a restriction digest or the like. In yet another embodiment, the fragment of the target sequence is amplified, and the detector oligonucleotide is contacted with either the amplified target nucleic acid itself or the amplified complementary strand of the target nucleic acid. In these embodiments, the detector oligonucleotide preferably is used in a heterologous format. That is, the detector oligonucleotide is reacted with a target nucleic acid, and the detector oligonucleotide that does not form a duplex with the target nucleic acid is washed before the cleavage sites are subject to cleavage.

In yet another embodiment, the detector oligonucleotide interacts with the target nucleic acid through an adaptor oligonucleotide. The adaptor oligonucleotide comprises a sequence that hybridizes with the target nucleic acid, and it comprises a separate portion that hybridizes to the detector oligonucleotide. The hybrid formed between the adaptor oligonucleotide and the detector oligonucleotide creates a template for polymerase extension of the detector oligonucleotide that makes the oligonucleotide double-stranded.

The detector oligonucleotide may be detected in a variety of ways known in the art either directly or after being rendered double-stranded. For example, but not by way of limitation, it may be detected by polyacrylamide gel electrophoresis on the basis of apparent molecular weight, by hybridization to a labeled probe, by solid phase capture using a detector oligonucleotide-specific probe or by cleavage with a restriction endonuclease.

EXAMPLES

The following examples are representative of the embodiments encompassed by the present invention and are not intended to limit the subject matter embraced by the present invention.

Example 1

SDA reactions may be performed using amplification primers and the detector oligonucleotide of the present invention. In this example, the detector is designed to detect a region of the HIV-1 pol gene. SDA may be carried out at about 52° C. in the presence of at least one, preferably 250, copies of a cloned, double-stranded DNA target nucleic acid using 500 nM amplification primers, 50 nM bumper primers and 200 nM detector oligonucleotide. Control reactions are carried out in the absence of the double-stranded target nucleic acid. Detectors are fluorescently labeled with multiple donor fluorophore/quencher fluorophore pairs (either Rhodamine/DABCYL or Fluorescein/DABCYL), which are separated by a BsoBI recognition sequence and are configured in close proximity. Donor fluorescence is monitored during the course of the reaction.

Donor fluorescence increases significantly during the course of the reaction when target DNA is present, indicating that the BsoBI restriction endonpclease site is cleaved. In contrast, in the absence of target DNA, fluorescence remains consistently low throughout the reaction.

Example 2

SDA reactions were performed using amplification primers and detector oligonucleotides of the present invention to detect HIV RNA transcript. SDA was carried out as follows: target buffer was prepared at 50 mM KOB, 120 mM bicine and was spiked with the RNA target nucleic acid at either 0 copies per reaction or 2000 copies per reaction. 65 µl of target buffer prepared with the indicated reagent concentrations was spotted into blank wells. 150 µl of sample buffer was dispensed into the target buffer wells, the solution was mixed, and the wells were placed at 50° C. for 20 minutes. RT reagent was prepared as indicated below.

| Reagent | [Stock] | Units | RT CONC. DESIRED | ADJ. CONC. | µl/rx | 24 | ADJUSTED VOLUME |
|---|---|---|---|---|---|---|---|
| RoDiH$_2$O | | | | | 29.35 | 704.40 | 810.1 |
| BSA | 5000 | c | 23.24 | 102.49 | 1.33 | 31.98 | 36.8 |
| DMSO | 100 | % | 8.04 | 35.46 | 23.05 | 553.12 | 636.1 |
| PAB CONC. | 20 | X | 0.12 | 0.51 | 1.67 | 40.00 | 46.0 |
| MG | 194 | mM | 6.50 | 28.67 | 9.60 | 230.50 | 265.1 |
| PAB MIX: ARALT.2 120 µM, 40 µM AL.1AV, bumpers 11.2 µM | | | | | | | |
| Total | | | | | 65.00 | 1560.00 | 1794.0 |
| NO RT | | | | | | | |
| RoDiH2O | | | | | 18.58 | 446.04 | 512.9 |
| BSA | 5000 | ng/µl | 32.89 | 131.54 | 1.32 | 31.57 | 36.3 |
| GLYCEROL | 70 | % | 8.00 | 32.00 | 22.86 | 548.57 | 630.9 |
| AMV-RT | 20 | units/µl | 0.1 | 0.40 | 1.00 | 24.00 | 27.6 |
| KP | 476.22 | mM | 5 | 20.00 | 2.10 | 50.40 | 58.0 |
| DTAG | 33.3 | mM | 0.50 | 2.02 | 3.03 | 72.65 | 83.5 |
| DCsTP | 96.8 | mM | 0.54 | 2.16 | 1.12 | 26.78 | 30.8 |
| Total | | | | | 50.00 | 1200.00 | 1380.0 |

150 µl of the solution in the heat spike wells was transferred to the RT wells for 5 minutes. The amplification mix was prepared as indicated below:

| Reagent | [Stock] | Units | RT CONC. DESIRED | ADJ. CON. | µl/rx | 24 | ADJUSTED VOLUME |
|---|---|---|---|---|---|---|---|
| RoDiH2O | | | | | 11.35 | 317.84 | 572.1 |
| KiPO4 | 476.22 | mM | 55.00 | 232.419 | 30.26 | 847.25 | 1525.1 |
| DMSO | 100 | % | 4.50 | 19.0161 | 11.79 | 330.12 | 594.2 |
| BSA | 5000 | ng/µl | 25.37 | 107.2176 | 1.33 | 37.23 | 67.0 |
| ADAPTER | 20 | X | 0.09 | 0.388774 | 1.21 | 33.75 | 60.7 |
| Detector | 200 | µM BD10 | 0.55 | 2.32419 | 0.72 | 20.17 | 36.3 |
| Bst | 17.25 | BDU | 0.18 | 0.760644 | 2.73 | 76.55 | 137.8 |
| BsoB1 | 22.08 | BDU | 0.22 | 0.929676 | 2.61 | 73.09 | 131.6 |
| Total | | | | | 62.00 | 1736.00 | 3124.8 |

The amplification mix was spotted into blank wells at 100 µl; and the wells were placed on a 60° C. heat block for 10 minutes prior to the completion of the 54° C. incubation. 62 µl of the amplification mix was transferred to the wells at the RT step, the wells were covered, and the plate was read using a PROBETEC fluorometer.

The detector oligonucleotide of the present invention was compared to hairpin probes. The results are shown below and in FIGS. 2A-2F. CTCGVnv3 is a hairpin probe; D=dabayl; R=rhodamine; the RDRD2.6B probe has 6 bases between the DABCYL and the rhodamine; the RDRD2.7B probe has 7 bases between the DABCYL and the rhodamine; and the RDRD2.8B probe has 8 bases between the DABCYL and the rhodamine.

Results:

| DETECTOR | COPIES/RXN | RESULTS | MEAN |
|---|---|---|---|
| 6B BETWEEN RDRD | 0 COPIES/RXN | 316 | 574 |
| | | 831 | |
| | 2,000 COPIES/RXN | 75305 | 73498 |
| | | 71691 | |
| 7B BETWEEN RDRD | 0 COPIES/RXN | 1678 | 2087 |
| | | 2495 | |
| | 2,000 COPIES/RXN | 77977 | 83393 |
| | | 88808 | |
| 8B BETWEEN RDRDR | 0 COPIES/RXN | 590 | 1003 |
| | | 1416 | |
| | 2,000 COPIES/RXN | 69174 | 72455 |
| | | 75736 | |
| RDRDR | 0 COPIES/RXN | 4145 | 3799 |
| | | 3452 | |
| | 2,000 COPIES/RXN | 53353 | 68919 |
| | | 84484 | |
| DRDRD | 0 COPIES/RXN | 3752 | 3213 |
| | | 2673 | |
| | 2,000 COPIES/RXN | 6263 | 5419 |
| | | 4575 | |
| CONTROL | 0 COPIES/RXN | 106 | 478 |
| | | 850 | |
| | 2,000 COPIES/RXN | 88644 | 94851 |
| | | 101058 | |

| Probe | CTGCUnv3 | DR | RDR | DRDRD | RDRDR | RDRD2.6B | RDRD2.7B | RDRD2.8B | RDDR.2 | DIMER |
|---|---|---|---|---|---|---|---|---|---|---|
| [Probe]/rx | 200 | 400 | 400 | 400 | 400 | 400 | 400 | 400 | 400 | 400/each |
| GC Target/rx | 1000 | 1000 | 1000 | 1000 | 1000 | 1000 | 1000 | 1000 | 1000 | 1000 |

-continued

| Probe | CTGCUnv3 | DR | RDR | DRDRD | RDRDR | RDRD2.6B | RDRD2.7B | RDRD2.8B | RDDR.2 | DIMER |
|---|---|---|---|---|---|---|---|---|---|---|
| Optics | Rox | Rox | Rox | Rox | Rox | Rox | Rox | Rox | Rox | Rox |
|  | 61590 | 49930 | 58250 | 4550 | 75870 | 29100 | 96390 | 62630 | 71330 | 1080 |
|  | 88050 | 70720 | 67890 | 3900 | 98700 | 45430 | 64280 | 98700 | 64250 | 180 |
|  | 60550 | 64190 | 66770 | 2760 | 97260 | 28950 | 108420 | 77870 | 52510 | 250 |
|  | 79580 | 77340 | 62470 | 4110 | 80320 | 36350 | 84510 | 95260 | 77470 | 10 |
|  | 76110 | 59680 | 58430 | 4350 | 82140 | 21580 | 66160 | 74770 | 56750 | 120 |
| Mean | 73176 | 64372 | 62762 | 3934 | 86858 | 32282 | 83952 | 81846 | 64462 | 328 |
| % CV | 16 | 16 | 7 | 18 | 12 | 28 | 23 | 18 | 16 | 131 |
| [Probe]/rx | 200 | 400 | 400 | 400 | 400 | 400 | 400 | 400 | 400 | 400/each |
| GC Target/rx | 0 | 0 | 0 | 0 | 0 | 0 | 0 | 0 | 0 | 0 |
| Optics | Rox | Rox | Rox | Rox | Rox | Rox | Rox | Rox | Rox | Rox |
|  | 70 | 940 | 1450 | 740 | 2630 | 1400 | 1350 | 1500 | 4120 | 110 |
|  | 80 | 470 | 20 | 1300 | 3090 | 1030 | 1500 | 2320 | 5800 | 220 |
|  | 460 | 930 | 2230 | 1660 | 1070 | 2070 | 460 | 620 | 8400 | 580 |
| Mean | 203 | 780 | 1233 | 1233 | 2263 | 1500 | 1103 | 1480 | 6107 | 303 |
| % CV | 109 | 34 | 91 | 38 | 47 | 35 | 51 | 57 | 35 | 81 |

The results demonstrate that a detector oligonucleotide of the present invention worked better than other probes, e.g., the CTGCUnv3 probe. The various detector oligonucleotide probe designs employed in Example 2 vary according to the number of bases between the rhodamine and DABCYL. The results also demonstrate that an improvement is observed when an additional base or two is added between the rhodamine and DABCYL moieties (see RDRD2.7B and RDRD2.8B).

From the above description, one skilled in the art can easily ascertain the essential characteristics of the present invention and, without departing from the spirit and scope thereof, can make various changes and modifications of the invention to adapt it to various usages and conditions.

What is claimed is:

1. A detector oligonucleotide, comprising at least two pairs of a donor fluorophore and quencher molecules, the donor fluorophore and quencher molecule being in close proximity such that otherwise detectable signal from said donor fluorophore is quenched by said quencher molecule, wherein said donor fluorophore and said quencher molecule in each said pair are separated by a cleavage site that is cleavable when hybridized to a target in a double-stranded form, and wherein cleavage at said cleavage site is capable of creating a detectable signal by the donor fluorophore that indicates the presence of a target nucleic acid.

2. A single-stranded first detector oligonucleotide and a single-stranded second oligonucleotide, wherein the first detector oligonucleotide comprises a plurality of pairs donor fluorophore and quencher molecules, wherein the donor fluorophore and quencher molecule in each said pair are separated by a cleavage site that is cleavable when hybridized to a target in a double-stranded form, and wherein the cleavage site is double-stranded when the first detector oligonucleotide forms a duplex with a second oligonucleotide that formed in the presence of a target nucleic acid.

3. The detector oligonucleotide of claim 2, wherein at least one said donor fluorophore is selected from the group consisting of fluorescein, sulforhodamine 101, pyrenebutanoate, acridine, ethenoadenosine, eosin, rhodamine, and erythrosine.

4. The oligonucleotide of claim 2, wherein at least one said quencher molecule is selected from the group consisting of DABCYL, DAMBI, DABSYL and methyl red.

5. The oligonucleotide of claim 2, wherein said donor fluorophores and said quencher molecules are separated by about 5 to 20 nucleic acid bases that comprise a cleavage site.

6. The oligonucleotide of claim 5, wherein said donor fluorophores and said quencher molecules are separated by about 6 to 8 nucleic acid bases that comprise a cleavage site.

7. The oligonucleotide of claim 2, wherein said cleavage site is cleavable by a chemical cleavage reagent.

8. The oligonucleotide of claim 2, wherein said cleavage site is cleavable by an endonuclease.

9. The oligonucleotide of claim 8, wherein said endonuclease is selected from the group consisting of Hinc II, Nci I, and BsoB1.

10. The oligonucleotide of claim 2, comprising ten pairs of one donor fluorophore and one quencher molecule.

11. The oligonucleotide of claim 10, comprising 50 pairs of one donor fluorophore and one quencher molecule.

12. The single-stranded first detector oligonucleotide of claim 2, wherein the first detector oligonucleotide comprises a first portion near the 5' terminus that is capable of forming a duplex with a first portion near the 3' terminus of the single-stranded second oligonucleotide of claim 2, wherein the second oligonucleotide comprises a second portion that is complementary to a target nucleic acid and a third portion near the 5' terminus of the single-stranded second oligonucleotide that comprises one strand of an endonuclease recognition site.

13. The oligonucleotide of claim 2, wherein said first detector oligonucleotide comprises a first portion capable of forming a duplex with a third oligonucleotide, wherein said third oligonucleotide comprises two portions: (1) a first portion having a sequence capable of forming a duplex with a target nucleic acid and (2) a second portion capable of forming a duplex with said first portion of said first detector oligonucleotide.

14. The detector oligonucleotide of claim 13, wherein said first portion is at the 5' terminus of said first detector oligonucleotide.

15. The oligonucleotide of claim 2, wherein said first detector oligonucleotide comprises a first portion capable of forming a duplex with a third oligonucleotide, wherein said third oligonucleotide comprises two portions: (1) a first portion having a sequence complementary to a target nucleic acid and (2) a second portion capable of forming a duplex with said first portion of said first detector oligonucleotide.

16. A partially double-stranded detector oligonucleotide, comprising a plurality of pairs of donor fluorophores and quencher molecule, wherein the donor fluorophore and quencher molecule in each said pair is in close proximity, wherein said donor fluorophore and said quencher molecule in each said pair is separated by a cleavage side, wherein said partially double-stranded detector oligonucleotide comprises a single-stranded portion that is capable of forming a duplex with a target nucleic acid.

17. The oligonucleotide of claim 16, wherein at least one of said cleavage sites is cleavable by a chemical cleavage reagent.

18. The oligonucleotide of claim 16, wherein at least one of said cleavage sites is cleavable by an endonuclease.

19. A kit, comprising a single-stranded first detector oligonucleotide, comprising a plurality of pairs of a donor fluorophores and a quencher molecules, wherein the donor fluorophore and quencher molecule are in close proximity, wherein said donor fluorophore and said quencher molecule in each said pair are separated by a cleavage site that is cleavable when hybridized to a target in a double-stranded form, and wherein the cleavage site is double-stranded when the first detector oligonucleotide forms a duplex with a second oligonucleotide capable of being formed in the presence of a target nucleic acid.

20. The kit of claim 19, further comprising an adapter oligonucleotide that comprises a first portion, which is capable of forming a duplex with the complement of a target oligonucleotide, and a second portion, the complement of which is capable of forming a duplex with the first portion of said detector oligonucleotide.

\* \* \* \* \*